(12) United States Patent
Tang et al.

(10) Patent No.: US 7,269,244 B2
(45) Date of Patent: Sep. 11, 2007

(54) METHODS AND APPARATUS FOR GENERATING THICK IMAGES IN CONE BEAM VOLUMETRIC CT

(75) Inventors: Xiangyang Tang, Waukesha, WI (US); Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/339,343

(22) Filed: Jan. 25, 2006

(65) Prior Publication Data
US 2007/0172019 A1    Jul. 26, 2007

(51) Int. Cl.
*H05G 1/60* (2006.01)

(52) U.S. Cl. .............. 378/19; 378/4; 378/901

(58) Field of Classification Search .......... 378/4–20, 378/210, 901
See application file for complete search history.

(56) References Cited

U.S. PATENT DOCUMENTS

| | | | |
|---|---|---|---|
| 5,034,304 A | 7/1991 | Feely | 430/270 |
| 5,270,654 A | 12/1993 | Feinberg et al. | 324/309 |
| 5,675,365 A | 10/1997 | Becerra et al. | 347/9 |
| RE35,656 E | 11/1997 | Feinberg et al. | 324/309 |
| 5,782,762 A | 7/1998 | Vining | 600/407 |
| 5,825,842 A * | 10/1998 | Taguchi | 378/15 |
| 5,926,521 A * | 7/1999 | Tam | 378/4 |
| 6,083,162 A | 7/2000 | Vining | 600/407 |
| 6,084,937 A * | 7/2000 | Tam et al. | 378/4 |
| 6,188,745 B1 * | 2/2001 | Gordon | 378/19 |
| 6,272,366 B1 | 8/2001 | Vining | 600/407 |
| 6,415,012 B1 * | 7/2002 | Taguchi et al. | 378/15 |
| 6,694,163 B1 | 2/2004 | Vining | 600/407 |
| 6,826,251 B1 * | 11/2004 | Miyazaki et al. | 378/15 |
| 6,909,913 B2 | 6/2005 | Vining | 600/407 |
| 2002/0141531 A1 * | 10/2002 | Taguchi | 378/19 |
| 2003/0099323 A1 * | 5/2003 | Nagata et al. | 378/4 |
| 2003/0219093 A1 * | 11/2003 | Hagiwara | 378/4 |

OTHER PUBLICATIONS

Tang et al., Cone Beam Backprojection (CB-FBP) Image Reconstruction by Tracking Re-sampled Projection Data, SPIE vol. 6318, 2006.*

* cited by examiner

*Primary Examiner*—Courtney Thomas
*Assistant Examiner*—Alexander Taningco
(74) *Attorney, Agent, or Firm*—Fisher Patent Group, LLC; Thomas M. Fisher

(57) ABSTRACT

A method includes performing a Cone Beam reconstruction of a thick image using a plurality of virtual planes.

18 Claims, 5 Drawing Sheets

METHODS AND APPARATUS FOR GENERATING THICK IMAGES IN CONE BEAM VOLUMETRIC CT

BACKGROUND OF THE INVENTION

This invention relates generally to methods and apparatus for computed tomography (CT), and more particularly to methods and apparatus for generating thick images in cone beam volumetric CT.

Generation of a tomographic image with a slice thickness larger than the nominal detector row width (referred to herein, as a "thick image") is of clinical importance in neuro- and trauma-CT imaging. A straightforward way to generate thick images is the weighted summation of tomographic images with the slice thickness equal to the detector row width (namely thin image) in the image domain. This approach generates a thick image with uniform slice thickness, but is computationally expensive because each thin image contributing to the thick image has to be reconstructed respectively in advance. Another way is to filter projection data along the z-direction, which is equivalent to increasing the nominal detector row width. This approach is computationally efficient, but may result in a non-uniform slice thickness. To have a balance between slice thickness uniformity and computational efficiency, an approach of generating a thick image using tracked and re-sampled virtual plane projection is disclosed below.

BRIEF DESCRIPTION OF THE INVENTION

In one aspect, a method is provided. The method includes performing a Cone Beam reconstruction of a thick image using a plurality of virtual planes.

In another aspect, a cone beam computed tomography (CT) system is provided. The system includes a radiation source configured to emit a cone beam of radiation, a detector positioned to receive the cone beam, and a computer coupled to the source and the detector. The computer is configured to perform a Cone Beam reconstruction of a thick image using a plurality of virtual planes.

In still another aspect, a computer readable medium is embedded with a program configured to instruct a computer to track a projection of a reconstruction plane (RP) in a detector and re-sample the tracked projection with $N_e$ virtual detector rows at a virtual detector row height $l_b$, wherein $N_e$ the effective number of physical detector rows occupied by the projection of the RP at $\beta=0°$ to reduce artifacts in a Cone Beam reconstruction of a thick image.

DETAILED DESCRIPTION OF THE INVENTION

Figure 1:
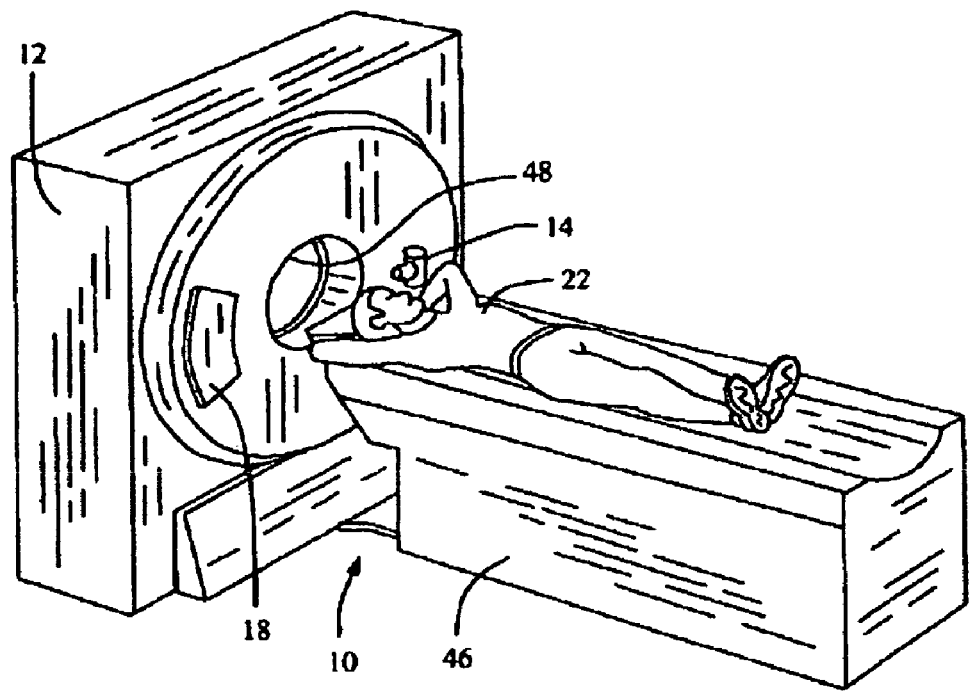
FIG. 1 is a pictorial view of a CT imaging system embodiment.

There are herein provided thick image generation methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
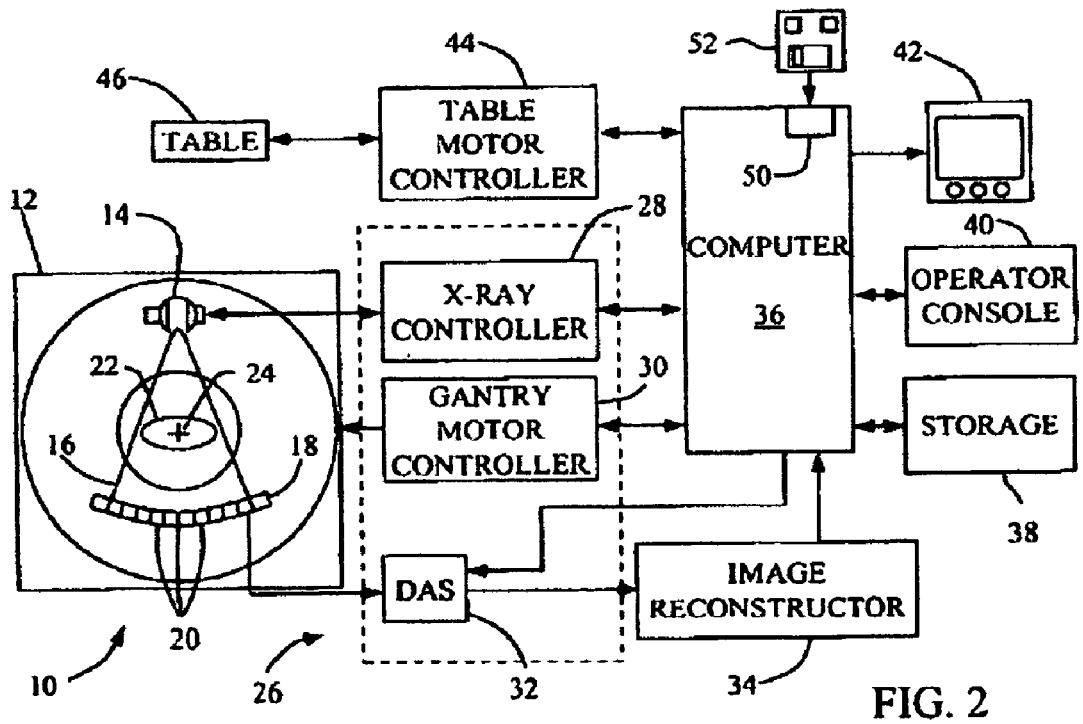
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

In one embodiment, CT system 10 is a Cone Beam Multi-Slice Computed Tomography (CT) System 10 in that radiation source 14 is configured to provide a Cone Beam (CB) of x-rays through object 22 and onto multislice detector array 18.

Figure 3:
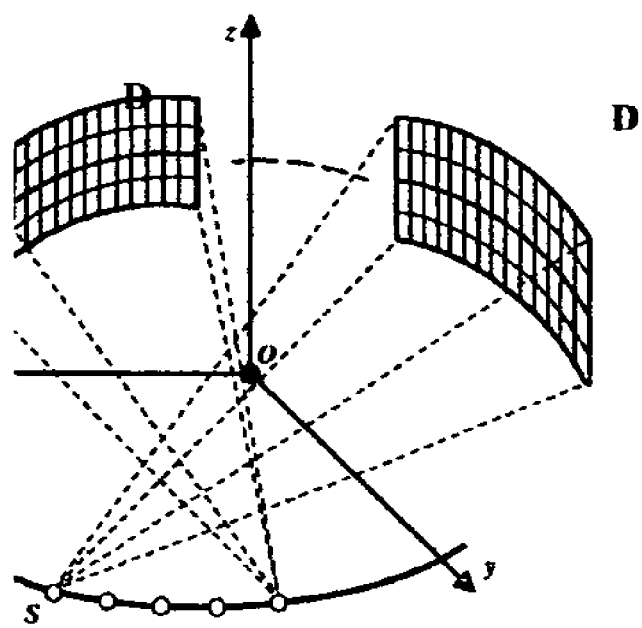
FIG. 3 illustrates the CB geometry for CT scanning and tomographic image reconstruction.
Figure 4:
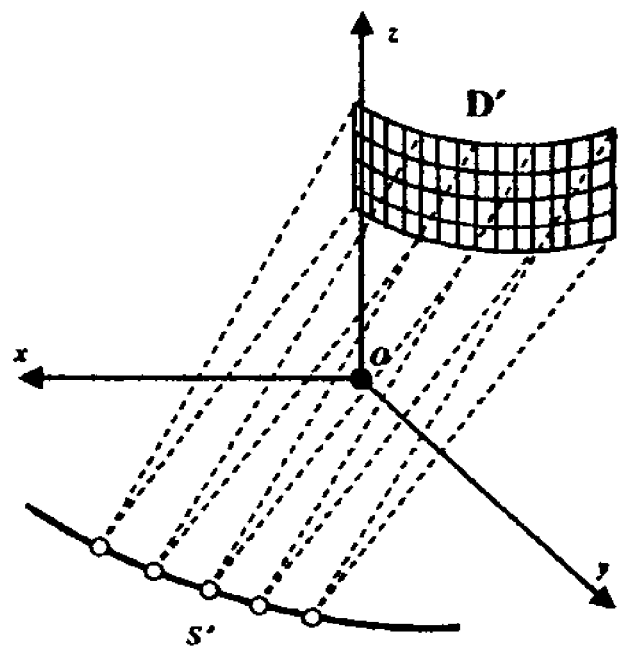
FIG. 4 illustrates the so-called cone-parallel geometry obtained from the CB geometry by row-wise fan-to-parallel rebinning.

The CB geometry for CT scanning and tomographic image reconstruction is shown in FIG. 3, while the so-called cone-parallel geometry obtained from the CB geometry by row-row fan-to-parallel rebinning is shown in FIG. 4. O-xyz is the coordinate system on which both the CB and cone-parallel geometries are defined. S and D represent the source focal spot and cylindrical detector respectfully in the CB geometry, while S' and D' represent the virtual source focal spot and detector respectfully in the cone-parallel geometry.

Figure 5:
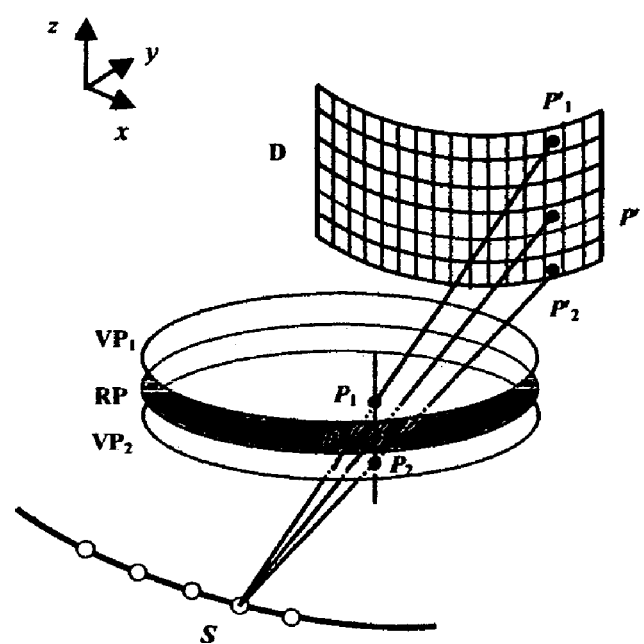
FIG. 5 illustrates schematically the weighted projection of virtual planes.

Taking the cone-parallel geometry as an example, the generation of a thick image via weighted projection of virtual planes is illustrated in the schematic diagram (FIG. 5), where (x, y, z) represents the coordinate of a point P(x, y, z) within the object to be reconstructed. Supposing P(x, y, 0) is within a reconstruction plane (RP) at z=0, its projection on detector D' is denoted as P'(x, y, 0). This means that point P(x, y, 0) is the intersection between the RP and the ray emanating from source focal spot S' and hitting the detector cell where P'(x, y, 0) locates at. In addition, suppose there is a virtual plane (VP) called $VP_1$ above RP at $z_1=d$, and another virtual reconstruction plane $VP_2$ under RP at $z_2=-d$. By drawing a straight line passing through point P(x, y, 0) and in parallel with the z-axis, one can get the intersections $P_1(x, y, d)$ and $P_2(x, y, -d)$ between the straight line and VP1 and VP2, respectively. By connecting the focal spot S' with $P_1(x, y, d)$ and $P_2(x, y, -d)$, one can get $P_1'(x, y, d)$ and $P_2'(x, y, -d)$, the projections of $P_1(x, y, d)$ and $P_2(x, y, -d)$ on detector D', respectively. By summing them together, the projection of points P, $P_1$ and $P_2$ in detector D' is obtained as shown in equation (1)

$$P''(x,y)=P'(x,y,0)+P_1'(x,y,-d)+P_2'(x,y,d) \quad (1)$$

One can use a family of VPs to obtain a very good approximation of the projection of line $P_1P_2$ by modifying equation (1) into:

$$P''(x, y) = \sum_{k=-K}^{k=K} P'(x, y, z_k) \quad (2)$$

where K represents the number of VPs on each side of the reconstruction plane RP at z=0. Apparently, the projection of line segments passing though other points in reconstruction plane RP at z=0 can be readily obtained by following the same logic illustrated above. Then, it is not hard to understand that, based on the summed projection data P''(x, y), a slab that is orthogonal to the z-axis and confined by virtual planes VP1 and VP2 with a slice thickness of 2d can be reconstructed using the 3D weighted CB-FBP (Filtered Backprojection) algorithm $$f(x, y, z) = \frac{\pi}{(\beta_{max} - \beta_{min})} \int_{\beta_{min}-o}^{\beta_{max}-o} \frac{R}{\sqrt{R^2 + Z^2}} w_{3d-k}(\alpha, \beta, t)\tilde{s}(\alpha, \beta, t)d\beta, \quad (3)$$

where $[\beta_{min}, \beta_{max}]=[0, 2\pi+\Delta\beta]$, $\tilde{s}$ is the filtered projection, and $$w_{3d-sum}(\alpha, \beta, t) = \frac{1}{2K+1} \sum_{k=-K}^{k=K} w_{3d-k}(\alpha, \beta, t) \quad (4)$$

i.e., the overall 3D weighting $w_{3d-sum}(\alpha, \beta, t)$ is the summation of the 3D weighting $w_{3d-k}(\alpha, \beta, t)$ corresponding to the RP at z=0 and each VP at $z=z_k$.

In practice, one can use a weighted version of equation (2) to get an even better approximation of the projection of line $P_1P_2$ $$P''(x, y) = \sum_{k=-K}^{k=K} w_k(x, y)P'(x, y, z_k), \quad (5)$$

as long as the weighting function $w_k(x, y)$ meets the normalization condition $$\frac{1}{2K+1} \sum_{k=-K}^{k=K} w_k(x, y) = 1.0 \quad (6)$$

Moreover, the distribution of the weighting function $w_k(x, y)$ over virtual planes $VP_k$ (k=-K, . . . 0, . . . , K) can be a Gaussian or other shapes to obtain a desired slice sensitivity profile (SSP) of a thick image.

Figure 6:
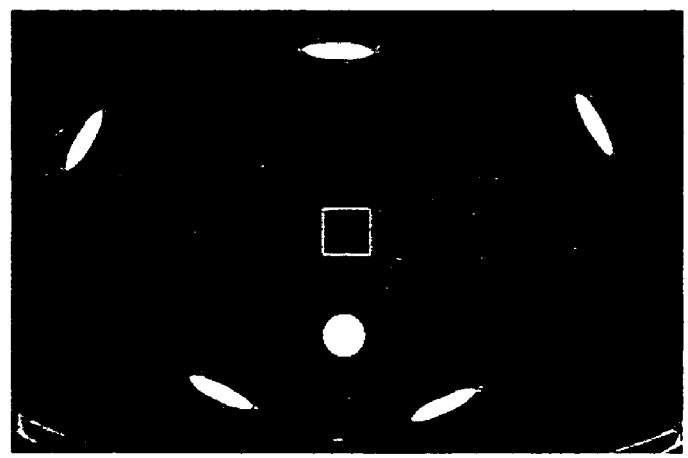
FIG. 6 illustrates a thick image with severe and unacceptable artifacts.
Figure 8:
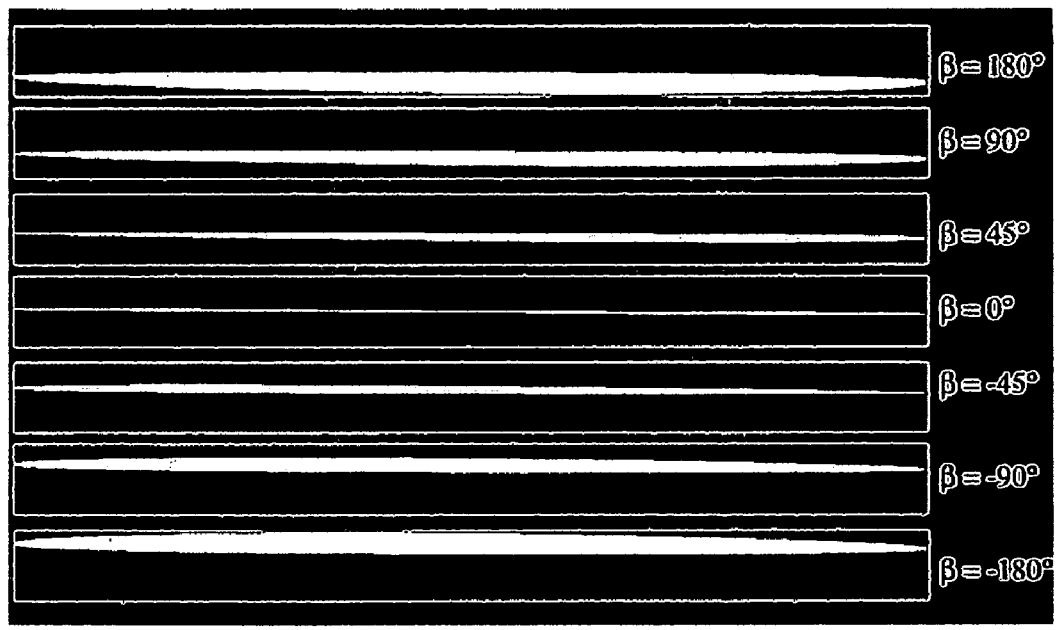
FIG. 8 illustrates projections of reconstruction plane RP on a detector with a dimension of 64×0.625 mm at various view angles $\beta$.

It is important to note that a direct application of equations (2)-(6) in detector D or virtual detector D' usually generates a thick image with severe and unacceptable artifacts as shown in FIG. 6. The root cause of the severe artifact is explained below. FIG. 8 shows projections of reconstruction plane RP on a detector with a dimension of 64×0.625 mm at various view angles ($\beta$=0°, ±45°, ±90° and ±180°). There exist intersection points between the rays connecting the source focal spot and detector cells and the reconstruction plane RP (namely intersection grid). By looking at equation (1) and FIG. 5 closely, it is not hard to understand that virtual planes VP1 and VP2 are sampled by the intersection grid. Moreover, it is not hard to understand that the intersection grid at $\beta$=0° is the sparsest and that at $\beta$=±180° is the densest, because the projections of reconstruction plane RP is the thinnest at $\beta$=0° and the thickest at $\beta$=±180°. To generate a thick image without artifacts, the spatial sampling rate of the intersection grid has to be sufficient over the view angle range [−180° 180°]. However, the very sparse intersection grid at $\beta$=0° cannot sample the virtual planes VP1 and VP2 at a sufficient spatial sampling rate, resulting in the severe artifacts existing in the thick image presented in FIG. 6.

Figure 9:
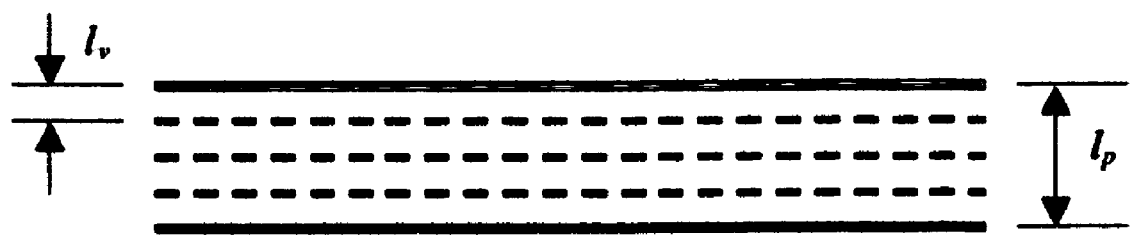
FIG. 9 schematically demonstrates an up-sampling process between a pair of physical rows.

One way to increase the sampling rate of the intersection grid is to up-sample the detector by inserting virtual detector rows between each pair of adjacent physical detector rows. In general, suppose there is a detector at the dimension of N×l mm, i.e., N physical rows with physical row height l mm. After the application of a factor F up-sampling, the detector dimension becomes F×N−(F−1))×(l/F) mm by inserting (F−1) virtual rows between each pair of adjacent physical rows. The up-sampling process between a pair of physical rows is schematically demonstrated in FIG. 9. Note that, once the factor F up-sampling is carried out, the number of total rows, including physical and virtual rows, and their row height become $$N_v = F \cdot N - F + 1 \quad (7)$$

and $$l_v = \frac{l}{F}, \quad (8)$$

respectively. For example, the physical detector at dimension of 64×0.625 mm becomes a virtual detector with a dimension of 253×0.15625 mm if the up-sampling factor F=4. Apparently, the number of total rows, including physical and virtual rows, increases proportionally with the up-sampling factor F, and such a significantly increased detector row number results in computational inefficiency in practice.

In fact, a factor F up-sampling over the whole detector is not necessary, since the projection of reconstruction plane RP usually occupies a portion of the detector over various view angle $\beta$ as shown in FIG. 8. If the detector rows occupied by the projection of reconstruction plane RP can be tracked, the number of total detector rows can be decreased dramatically, which results in significantly improved computational efficiency. Based on the arguments aforementioned, a general approach to generate thick image in CB reconstruction using virtual planes is:

(a) Determining $N_e$, the effective number of physical detector rows occupied by the projection of reconstruction plane RP at $\beta$=0°;

(b) Determining the up-sampling factor F and its associated virtual sampling rate $l_0$ to have an adequate intersection gird $\beta$=0°;

(c) Letting the virtual detector row height be a monotonically increasing function of the magnitude of view angle $\beta$, i.e., $$l_{\beta_1} < l_{\beta_2} \text{ while } |\beta_1| < |\beta_2| \quad (9)$$

For example, the virtual detector row height can be in the form $$l_\beta = \left(\frac{l}{F}\right) \cdot \left(1 + \frac{\eta|\beta|}{180}\right) \quad (10)$$

where $\eta$ is a coefficient to adjust the intersection gird of reconstruction plane RP with adequate sampling rate at view angle $\beta$.

(d) Tracking the projection of reconstruction plane RP in the detector and re-sample the tracked projection with $N_e$ virtual detector rows at virtual detector row height $l_\beta$.

Figure 7:
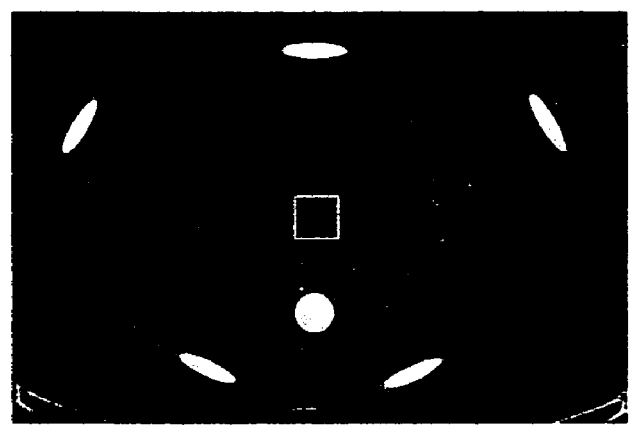
FIG. 7 illustrates an image reconstructed by equations (1)-(6) based on the strategies specified by (a)-(d).

To evaluate the disclosed approach, an image reconstructed by equations (1)-(6) based on the strategies specified by (a)-(d) is presented in FIG. 7. The severe artifacts existing in FIG. 6 have been eliminated by the projection tracking and re-sampling technique disclosed here. In the evaluation, the detector dimension is 16×1.25 mm and F=4, $\eta$=2.0 and $d_1$=$d_2$=1.25 mm are utilized.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method comprising:
performing a Cone Beam reconstruction of a thick image using a plurality of virtual planes; and
tracking a projection of a reconstruction plane (RP) in a detector and re-sampling the tracked projection with $N_e$ virtual detector rows at a virtual detector row height $l_\beta$, wherein $N_e$ the effective number of physical detector rows occupied by the projection of the RP at $\beta$=0° to reduce artifacts.

2. A method in accordance with claim 1 further comprising determining a virtual detector row height as a function of a magnitude of a view angle $\beta$.

3. A method in accordance with claim 2 wherein said determining comprises determining the virtual detector row height as a monotonic function of the magnitude of the view angle $\beta$.

4. A method in accordance with claim 3 wherein said determining comprises determining the virtual detector row height as a monotonically increasing function of the magnitude of the view angle $\beta$.

5. A method in accordance with claim 4 further comprising determining an up-sampling factor F and an associated virtual sampling rate $l_0$ for view angle $\beta$=0° such that artifact reduction occurs.

6. A method in accordance with claim 1 further comprising determining an up-sampling factor F and an associated virtual sampling rate $l_0$ for view angle $\beta$=0° such that artifact reduction occurs.

7. A method in accordance with claim 1 wherein the virtual detector row height $l_\beta$ is a monotonically increasing function of the magnitude of the view angle $\beta$.

8. A cone beam computed tomography (CT) system comprising:
a radiation source configured to emit a cone beam of radiation;
a detector positioned to receive the cone beam; and
a computer coupled to said source and detector, said computer configured to:
perform a Cone Beam reconstruction of a thick image using a plurality of virtual planes; and
track a projection of a reconstruction plane (RP) in a detector and re-sample the tracked projection with $N_e$ virtual detector rows at a virtual detector row height $l_\beta$, wherein $N_e$ the effective number of physical detector rows occupied by the projection of the RP at $\beta$=0° to reduce artifacts.

9. A system in accordance with claim 8 wherein said computer further configured to determine a virtual detector row height as a function of a magnitude of a view angle $\beta$.

10. A system in accordance with claim 9 wherein said computer further configured to determine the virtual detector row height as a monotonic function of the magnitude of the view angle $\beta$.

11. A system in accordance with claim 10 wherein said computer further configured to determine the virtual detector row height as a monotonically increasing function of the magnitude of the view angle $\beta$.

12. A system in accordance with claim 11 wherein said computer further configured to determine an up-sampling factor F and an associated virtual sampling rate $l_0$ for view angle $\beta$=0° such that artifact reduction occurs.

13. A system in accordance with claim 8 wherein the virtual detector row height $l_\beta$ is a monotonically increasing function of the magnitude of the view angle $\beta$.

14. A computer readable medium embedded with a program configured to instruct a computer to track a projection of a reconstruction plane (RP) in a detector and re-sample the tracked projection with $N_e$ virtual detector rows at a virtual detector row height $l_\beta$, wherein $N_e$ the effective number of physical detector rows occupied by the projection of the RP at $\beta$=0° to reduce artifacts in a Cone Beam reconstruction of a thick image.

15. A computer readable medium in accordance with claim 14 wherein said program is further configured to instruct the computer to perform the Cone Beam reconstruction of a thick image using a plurality of virtual planes.

16. A computer readable medium in accordance with claim 15 wherein the virtual detector row height $l_\beta$ is a monotonically increasing function of the magnitude of the view angle $\beta$.

17. A computer readable medium in accordance with claim 14 wherein the virtual detector row height $l_\beta$ is a monotonic function of the magnitude of the view angle $\beta$.

18. A computer readable medium in accordance with claim 17 wherein the virtual detector row height $l_\beta$ is a monotonically increasing function of the magnitude of the view angle $\beta$.

* * * * *